(12) United States Patent
DiCarlo et al.

(10) Patent No.: US 11,013,551 B2
(45) Date of Patent: May 25, 2021

(54) METHOD FOR ABLATING TISSUE WITH MULTIPLE ABLATION PROBES

(71) Applicant: Boston Scientific Scimed, Inc., Maple Grove, MN (US)

(72) Inventors: Paul DiCarlo, Middleboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 326 days.

(21) Appl. No.: 16/105,473

(22) Filed: Aug. 20, 2018

(65) Prior Publication Data

US 2019/0000527 A1 Jan. 3, 2019

Related U.S. Application Data

(60) Continuation of application No. 14/469,267, filed on Aug. 26, 2014, now Pat. No. 10,052,148, which is a continuation of application No. 12/573,031, filed on Oct. 2, 2009, now Pat. No. 8,814,855, which is a division of application No. 11/073,917, filed on Mar. 7, 2005, now Pat. No. 7,601,149.

(51) Int. Cl.
*A61B 18/14* (2006.01)
*A61B 18/12* (2006.01)

(52) U.S. Cl.
CPC .......... *A61B 18/14* (2013.01); *A61B 18/1206* (2013.01); *A61B 18/1477* (2013.01); *A61B 2018/124* (2013.01); *A61B 2018/1273* (2013.01); *A61B 2018/1425* (2013.01); *A61B 2560/0214* (2013.01)

(58) Field of Classification Search
CPC . A61B 18/1206; A61B 18/14; A61B 18/1477; A61B 18/124; A61B 18/1273; A61B 18/1425; A61B 2560/0214
See application file for complete search history.

(56) References Cited

U.S. PATENT DOCUMENTS

| | | | |
|---|---|---|---|
| 4,244,371 A | 1/1981 | Farin | |
| 5,019,034 A | 5/1991 | Weaver et al. | |
| 5,342,356 A | 8/1994 | Ellman et al. | |
| 5,458,597 A | 10/1995 | Edwards et al. | |

(Continued)

FOREIGN PATENT DOCUMENTS

WO 9629946 10/1996

OTHER PUBLICATIONS

"File History," for U.S. Appl. No. 11/073,917.

(Continued)

*Primary Examiner* — Michael F Peffley
(74) *Attorney, Agent, or Firm* — Pauly, DeVries Smith & Deffner LLC

(57) ABSTRACT

A tissue ablation system comprises an ablation source, such as an RF ablation source, configured for generating a common power signal, and a power multiplexor configured for splitting the power signal into first and second power signals, substantially attenuating the second power signal relative to the first power signal to create nominal and attenuated power signals, and sequentially delivering the nominal power signal to each tissue ablation probe, while delivering the attenuated power signal to the remaining ablation probes to which the nominal power signal is currently not delivered.

15 Claims, 9 Drawing Sheets

(56) References Cited

U.S. PATENT DOCUMENTS

| | | |
|---|---|---|
| 5,496,312 A | 3/1996 | Klicek |
| 5,683,384 A | 11/1997 | Gough et al. |
| 5,718,246 A | 2/1998 | Vona |
| 6,010,613 A | 1/2000 | Walters et al. |
| 6,043,066 A | 3/2000 | Mangano et al. |
| 6,090,105 A | 7/2000 | Zepeda et al. |
| 6,235,023 B1 | 5/2001 | Lee et al. |
| 6,346,104 B2 * | 2/2002 | Daly .................. A61B 18/1477 606/34 |
| 6,379,353 B1 | 4/2002 | Nichols et al. |
| 6,405,732 B1 | 6/2002 | Utley et al. |
| 6,620,157 B1 | 9/2003 | Quick et al. |
| 6,623,423 B2 | 9/2003 | Sakurai et al. |
| 6,638,277 B2 | 10/2003 | Schaefer et al. |
| 6,889,089 B2 | 5/2005 | Behl et al. |
| 6,912,417 B1 | 6/2005 | Bernard et al. |
| 6,958,064 B2 * | 10/2005 | Rioux .................. A61B 18/148 606/41 |
| 7,195,629 B2 | 3/2007 | Behl et al. |
| 7,252,664 B2 | 8/2007 | Nasab et al. |
| 7,282,049 B2 * | 10/2007 | Orszulak ............ A61B 18/1206 606/34 |
| 7,456,012 B2 | 11/2008 | Ryttsén et al. |
| 7,601,149 B2 | 10/2009 | Dicarlo et al. |
| 8,014,854 B2 | 9/2011 | Kroll et al. |
| 8,114,070 B2 | 2/2012 | Rubinsky et al. |
| 8,251,986 B2 | 8/2012 | Chornenky et al. |
| 8,282,631 B2 | 10/2012 | Rubinsky et al. |
| 8,540,710 B2 | 9/2013 | Johnson et al. |
| 8,647,338 B2 | 2/2014 | Chornenky et al. |
| 8,814,855 B2 | 8/2014 | Dicarlo et al. |
| 8,926,606 B2 | 1/2015 | Arena et al. |
| 10,052,148 B2 | 8/2018 | Dicarlo et al. |
| 2001/0020166 A1 | 9/2001 | Daly et al. |
| 2001/0044596 A1 | 11/2001 | Jaafar et al. |
| 2002/0022864 A1 | 2/2002 | Mahvi et al. |
| 2002/0111608 A1 | 8/2002 | Baerveldt et al. |
| 2002/0111615 A1 * | 8/2002 | Cosman ............. A61B 18/1482 606/41 |
| 2002/0156472 A1 | 10/2002 | Lee et al. |
| 2004/0006337 A1 | 1/2004 | Nasab et al. |
| 2004/0138653 A1 | 7/2004 | Dabney et al. |
| 2004/0267256 A1 | 12/2004 | Garabedian et al. |
| 2005/0080409 A1 | 4/2005 | Young et al. |
| 2005/0107781 A1 | 5/2005 | Ostrovsky et al. |
| 2006/0200120 A1 | 9/2006 | Dicarlo et al. |
| 2010/0023002 A1 | 1/2010 | Dicarlo et al. |
| 2014/0364850 A1 | 12/2014 | Dicarlo et al. |

OTHER PUBLICATIONS

"File History," for U.S. Appl. No. 12/573,031.
"File History," for U.S. Appl. No. 14/469,267.
"International Preliminary Report on Patentability," for PCT Application No. PCT/US2006/007492 dated Sep. 20, 2007 (7 pages).
"International Search Report and Written Opinion," for PCT Application No. PCT/US2006/007492 dated Jul. 25, 2006 (9 pages).

\* cited by examiner

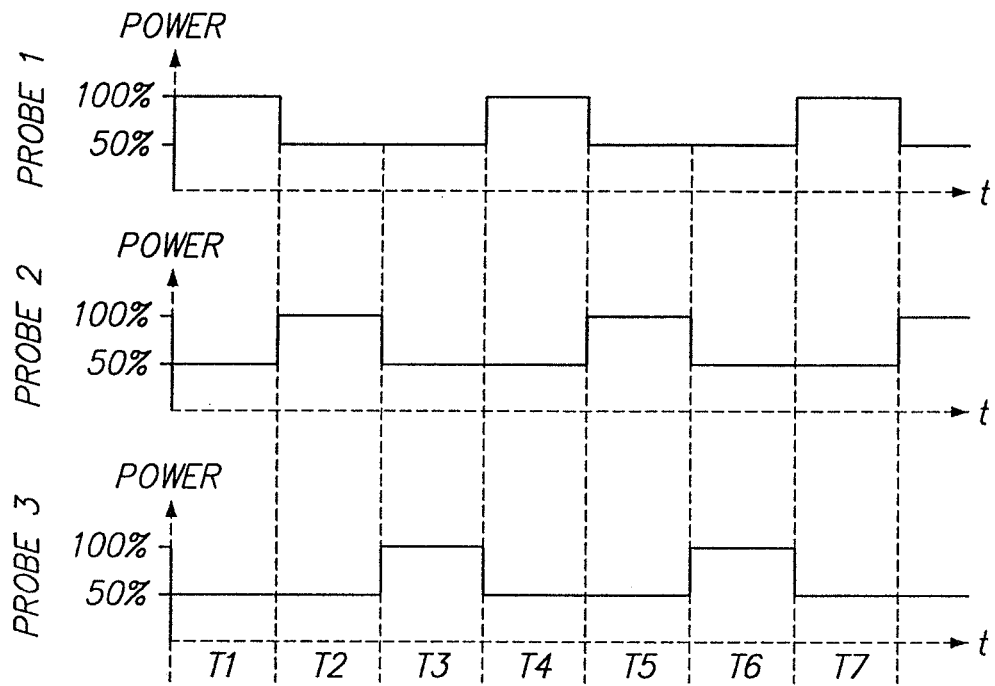

|         | PROBE 1 | PROBE 2 | PROBE 3 | PROBE 4 | PROBE 5 | PROBE 6 |
|---------|---------|---------|---------|---------|---------|---------|
| STATE 1 | UNATT   | ATT     | ATT     | ATT     | ATT     | ATT     |
| STATE 2 | ATT     | UNATT   | ATT     | ATT     | ATT     | ATT     |
| STATE 3 | ATT     | ATT     | UNATT   | ATT     | ATT     | ATT     |
| STATE 4 | ATT     | ATT     | ATT     | UNATT   | ATT     | ATT     |
| STATE 5 | ATT     | ATT     | ATT     | ATT     | UNATT   | ATT     |
| STATE 6 | ATT     | ATT     | ATT     | ATT     | ATT     | UNATT   |

METHOD FOR ABLATING TISSUE WITH MULTIPLE ABLATION PROBES

This application is a Continuation of U.S. patent application Ser. No. 14/469,267, filed Aug. 26, 2014, now U.S. Pat. No. 10,052,148, which is a Continuation of U.S. patent application Ser. No. 12/573,031, filed Oct. 2, 2009, now U.S. Pat. No. 8,814,855, which is a Divisional of U.S. application Ser. No. 11/073,917 filed on Mar. 7, 2005, now issued as U.S. Pat. No. 7,601,149, the contents of which are incorporated by reference in their entirety.

FIELD OF THE INVENTION

The invention relates generally to the structure and use of radiofrequency electrosurgical apparatus for the treatment of tissue. More particularly, the invention relates to an electrosurgical system having multiple ablation probes to treat large volumes of tissue, particularly for the treatment of tumors in the liver and other tissues and organs.

BACKGROUND

The delivery of radio frequency (RF) energy to target regions within tissue is known for a variety of purposes of particular interest to the present invention(s). In one particular application, RF energy may be delivered to diseased regions (e.g., tumors) for the purpose of ablating predictable volumes of tissue with minimal patient trauma. RF ablation of tumors is currently performed using one of two core technologies.

The first technology uses a single needle electrode, which when attached to a RF generator, emits RF energy from the exposed, non-insulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. PCT application WO 96/29946 and U.S. Pat. No. 6,379,353 disclose such probes. In U.S. Pat. No. 6,379,353, a probe system comprises a cannula having a needle electrode array reciprocatably mounted therein. The individual electrodes within the array have spring memory, so that they assume a radially outward, arcuate configuration as they are advanced distally from the cannula. In general, a multiple electrode array creates a larger lesion than that created by a single needle electrode.

In theory, RF ablation can be used to sculpt precisely the volume of necrosis to match the extent of the tumor. By varying the power output and the type of electrical waveform, it is possible to control the extent of heating, and thus, the resulting ablation. However, the size of tissue coagulation created from a single electrode, and to a lesser extent a multiple electrode array, has been limited by heat dispersion. As a consequence, when ablating lesions that are larger than the capability of the above-mentioned devices, the common practice is to stack ablations (i.e., perform multiple ablations) within a given area. This requires multiple electrode placements and ablations facilitated by the use of ultrasound imaging to visualize the electrode in relation to the target tissue. Because of the echogenic cloud created by the ablated tissue, however, this process often becomes difficult to accurately perform. This process considerably increases treatment duration and patent discomfort and requires significant skill for meticulous precision of probe placement.

In response to this, the marketplace has attempted to create larger lesions with a single probe insertion. Increasing generator output, however, has been generally unsuccessful for increasing lesion diameter, because an increased wattage is associated with a local increase of temperature to more than 100_degree_C., which induces tissue vaporization and charring. This then increases local tissue impedance, limiting RF deposition, and therefore heat diffusion and associated coagulation necrosis. In addition, patient tolerance appears to be at the maximum using currently available 200 W generators.

To a large extent, the size and nature of an ablation lesion depends on how the electrode element(s) are arranged. In one arrangement, RF current may be delivered to an electrode element (whether a single electrode or electrode array) in a monopolar fashion, which means that current will pass from the electrode element to a dispersive electrode attached externally to the patient, e.g., using a contact pad placed on the patient's flank. In another arrangement, the RF current is delivered to two electrode elements in a bipolar fashion, which means that current will pass between "positive" and "negative" electrode elements. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrode arrays generally create larger and/or more efficient lesions than monopolar electrode arrays. To provide even larger lesions, it is known to operate two electrode arrays in a bipolar arrangement.

Thus, to a certain extent, the use of bipolar electrode arrangements has eliminated the need to "stack" ablations when treating a tumor. The ability to provide uniform heating and the creation of homogenous tissue lesions, however, is particularly difficult with bipolar devices. For example, the two bipolar electrodes may be placed in regions with quite different perfusion characteristics, and the heating around each pole can be quite different. That is, one pole may be located adjacent to a large blood vessel, while the other pole may be located adjacent to tissue, which is less perfused. Thus, the pole located in the less perfused tissue will heat the tissue immediately surrounding the electrode much more rapidly than the tissue surrounding the opposite polar electrode is heated. In such circumstances, the tissue surrounding one pole may be preferentially heated and necrosed, while the tissue surrounding the other pole will neither be heated nor necrosed sufficiently.

In the case where two electrode arrays are used, if the distance between the electrode arrays is too great in an attempt to ablate a longer tissue volume, the energy transmitted between the electrode arrays may thin and not fully ablate the intermediate tissue. As a result, an hour-glass shaped ablation, rather than the desired uniform circular/elliptical ablation, may be created. Also, because the electrode arrays are, in effect, three-dimensional, portions between the electrode arrays will be closer together than other portions of the electrode arrays, thereby causing a non-uniform current density between the electrode arrays, resulting in a non-uniform ablation. Besides lacking the ability to produce predictable homogenous lesions, bipolar arrangements, which are designed to ablate tissue between the electrodes, are not well-suited for simultaneously ablating multiple tissue regions.

In situations where it is desired to produce large homogenous lesions or simultaneously ablate multiple tissue regions, it is known to arrange multiple probes in a monopolar fashion (i.e., the RF energy generated by each probe is conveyed to a dispersive electrode attached to the skin of the patient. In this case, current flows from each probe to the ground pad. A drawback to this approach is that simultaneously supplying power to multiple probes taxes the power output by the RF generator, which may cause insufficient heating around the probes. Also, because the tissue adjacent the probes is non-uniform (e.g., one probe may be adjacent a blood vessel), the heating pattern created by the probes will be non-uniform, thereby making it difficult to predict the nature of the resulting lesion.

To address these drawbacks, it is known to use an ablation system that sequentially switches ablation energy between probes, so that at any given time, ablation energy is supplied to only one probe. While this switching technique may result in a more efficient and predictable lesion, it is believed that, during any given time period, the tissue adjacent the probes to which the ablation energy is not currently supplied temporarily cools—especially when the switching speed between the probes is relatively slow, e.g., a few seconds. As a result, the cooled tissue must be reheated when power is again supplied to the adjacent probes, thereby losing some efficiency in the ablation process.

For this reason, it would be desirable to provide improved multi-probe electrosurgical methods and systems for more efficiently ablating tumors in the liver and other body organs.

SUMMARY OF THE INVENTION

In accordance with a first aspect of the present inventions, a tissue ablation system is provided. The tissue ablation system comprises an ablation source, such as a radio frequency (RF) source, having a common power output. The tissue ablation system further comprises a power splitter having a splitter input and first and second splitter outputs. The splitter input is coupled to the common power output. In one embodiment, the first and second splitter outputs are substantially unattenuated relative to the common power output, although it should be noted that the present inventions should not be so limited. For example, an intervening attenuation device, whatever its nature, can be placed between the common power output and the first and second splitter inputs, so that the first and second splitter outputs are both attenuated relative to the common power output.

The tissue ablation system further comprises a power attenuator having an attenuator input and an attenuator output. The attenuator input is coupled to the second splitter output. In one embodiment, the attenuator is configured for attenuating power at a level equal to or greater than 3 dB, e.g., within the range of 3 dB to 6 dB. Although the attenuator may be fixed in one embodiment, the attenuator may be variable in alternative embodiments. For example, the attenuation value of the attenuator may be capable of being set by the user. As another example, the tissue ablation system may further comprise a feedback control circuit configured for receiving a feedback input (e.g., a measured physiological parameter, such as tissue impedance or temperature) and for varying the attenuation value of the attenuator based on the feedback input.

The tissue ablation system further comprises a switch having first and second switch inputs and a plurality of switch outputs. The first switch input is coupled to the first splitter output and the second switch input is coupled to the attenuator output. The plurality of switch outputs are coupleable or coupled to a plurality of tissue ablation probes, which may be included within the tissue ablation system. In one embodiment, the plurality of switch outputs comprises at least three outputs to accommodate at least three ablation probes, although other plural numbers of switch outputs can be used including just two.

The switch is configured for sequentially coupling the first switch input (which is coupled to the first splitter output) to each one of the switch outputs, while coupling the second switch input (which is coupled to the attenuator output) to the switch output currently not coupled to the first switch input. Although the present inventions should not be so limited in their broadest aspects, this configuration allows the power to be continuously delivered to each ablation probe—albeit sometimes at an attenuated level.

The switch may be configured for sequentially coupling the first switch input to each switch output at a fixed rate. Preferably, this fixed switching rate is greater than once per second to maximize the ablation efficiency of the system, but less than thirty seconds to prevent tissue charring. It should be noted, however, that the present inventions in their broadest aspects should not be so limited. As such, the fixed switching rate may be less than once per one second or greater than once per thirty seconds if desirable. The switch may alternatively be configured for sequentially coupling the first switch input to each switch output at a variable rate. For example, the tissue ablation system may further comprise a feedback control circuit configured for receiving a feedback input (e.g., a measured physiological parameter, such as tissue impedance or temperature) and controlling the switch to couple the first splitter output to each switch output based on the feedback input.

Notably, for the purposes of this specification, two elements that are coupled or coupleable together does not necessarily mean that the two elements must be connected together. Rather, the one element need only be capable of receiving power or derivation of that power from that other element. Thus, the two elements may be coupled or coupleable together even though an intervening element exists between the two elements.

In accordance with a second aspect of the present inventions, another tissue ablation system is provided. The tissue ablation system comprises an ablation source, such as an RF ablation source, configured for generating a common power signal. The tissue ablation system further comprises a power multiplexor configured for splitting the power signal into first and second power signals, and substantially attenuating the second power signal relative to the first power signal. In one embodiment, the first power signal is substantially unattenuated relative to the common power signal, although it should be noted that the present inventions should not be so limited. For example, an intervening attenuation device can be used to attenuate the first and second power signals after they are output by the ablation source.

In one embodiment, the power multiplexor is configured for attenuating power at a level equal to or greater than 3 dB, e.g., within the range of 3 dB to 6 dB. In an optional embodiment, the power multiplexor is configured for varying the value that the second power signal is attenuated. In this case, the power multiplexor may optionally be configured for receiving a feedback input (e.g., a measured physiological parameter, such as tissue impedance or temperature) and varying the attenuation value based on the feedback input.

The power multiplexor is further configured for delivering the first power signal to one or more of a plurality of tissue ablation probes (which may be included within the tissue ablation system), while delivering the second power signal to a different one or more of the plurality of ablation probes. The power multiplexor may be configured for varying the number of tissue ablation probes to which it delivers the first and second power signals. In this manner, the tissue ablation system can be adapted to any number of tissue ablation probes desired to be used.

By way of non-limiting example, the power multiplexor may be configured for sequentially delivering the first power signal to different sets of the tissue ablation probes, while delivering the second power signal to the tissue ablation probes to which the first power signal is not currently delivered. The set of the tissue ablation probes to which the first power signal is sequentially delivered can equal any value, but in the preferred embodiment, the probe set only comprises a single tissue ablation probe in order to focus more of the ablation energy towards a single tissue ablation probe at a time. The plurality of tissue ablation probes may equal any plurality number, including just two ablation probes, but in one embodiment, comprises at least three tissue ablation probes.

If the first power signal is sequentially delivered, the power multiplexor may be configured for sequentially deliver it to each tissue ablation probe at a fixed rate. Preferably, this fixed rate is greater than one probe per second to maximize the ablation efficiency of the system, but less than one probe per thirty seconds to prevent tissue charring. It should be noted, however, that the present inventions in their broadest aspects should not be so limited. As such, the fixed rate may be less than one probe per one second or greater than one probe per thirty seconds if desirable. The power multiplexor may alternatively be configured for sequentially coupling the first power signal to each tissue ablation probe at a variable rate. For example, the power multiplexor may be configured for receiving a feedback input (e.g., a measured physiological parameter, such as tissue impedance or temperature) and delivering the first power signal to each tissue ablation probe based on the feedback input.

In accordance with a third aspect of the present inventions, a method of treating tissue within a patient is provided. The method comprises introducing a plurality of probes into the patient. In one method, the probes are percutaneously introduced into the patient, although the probes may alternatively be intravascularly introduced into the patient or introduced through an open surgical incision. In one method, at least three ablation probes are used, although other plural numbers of probes can be used, including just two.

The method further comprises sequentially delivering nominal ablation energy (e.g., RF ablation energy) to each of a plurality of probes, while delivering attenuated ablation energy to a remainder of the plurality of probes. The nominal ablation energy may or may not be attenuated. However, the attenuated ablation energy has an amplitude that is substantially less than the amplitude of the nominal ablation energy. For example, the amplitude of the attenuated ablation energy may be equal to or greater than 3 dB below the amplitude of the nominal ablation energy, e.g., within the range of 3 to 6 dB.

The nominal ablation energy may be sequentially delivered to each probe at a fixed rate. Preferably, this fixed rate is greater than one probe per second to maximize the ablation efficiency of the system, but less than thirty seconds to prevent tissue charring. It should be noted, however, that the present inventions in their broadest aspects should not be so limited. As such, the fixed rate may be less than one probe per one second or greater than one probe per thirty seconds if desirable. The nominal ablation energy may alternatively be sequentially delivered to each probe at a variable rate. For example, a physiological parameter, e.g., a tissue impedance or temperature, can be measured, in which case, the nominal ablation energy can be sequentially delivered to the probes based on the measured physiological parameters.

In one method, the nominal ablation energy and attenuated ablation energy are derived from a single ablation source. In alternative methods, the nominal ablation energy and attenuated ablation energy can be derived from multiple ablation sources. The amplitude of the attenuated ablation energy may be variably set, e.g., by measuring a physiological feedback parameter and setting the amplitude based thereon, or even by manually setting the amplitude.

The method further comprises ablating the tissue with the nominal ablation energy and attenuated ablation energy. The tissue may be any tissue that can be treated with ablation energy, e.g., one or more tumors. In one method, the tissue is distributed amongst a plurality of treatment regions, but may also be contained within a single treatment region.

In accordance with a fourth aspect of the present inventions, another method of treating tissue within a patient is provided. The method comprises introducing a plurality of probes into the patient, which may be accomplished in the same manner described above. The method further comprises delivering nominal ablation energy (e.g., RF ablation energy) to one or more of the ablation probes, while delivering attenuated ablation energy to a different one or more of the ablation probes, and ablating the tissue with the nominal ablation energy and attenuated ablation energy. The detailed features of this method may be the similar to those described above, with the exception that, in one embodiment, the first power signal may be sequentially delivered to more than one tissue ablation probe at a time.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 4 is a timing diagram illustrating the switching of ablation energy between tissue ablation probes used in the tissue ablation system of FIG. 1;

FIG. 5 is a table illustrating the ablation states in which the plurality of tissue ablation probes used in the tissue ablation system of FIG. 1 can be placed;

DETAILED DESCRIPTION OF THE ILLUSTRATED EMBODIMENTS

Figure 1:
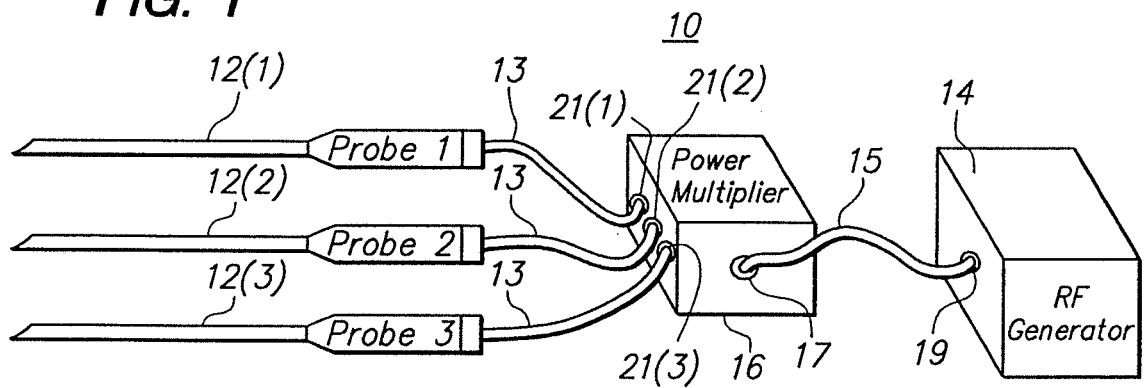
FIG. 1 is a perspective view of a tissue ablation system constructed in accordance with a preferred embodiment of the present invention.

Referring generally to FIG. 1, a tissue ablation system 10 constructed in accordance with one embodiment of the present inventions will be described. The tissue ablation system 10 generally includes a plurality of tissue ablation probes 12 (in this case, three probes 12(1)-(3)) for introduction into the body of a patient for ablative treatment of target tissue, a radio frequency (RF) generator 14 configured for generating RF power, and a power multiplexor 16 configured for receiving the RF power from the RF generator via a standard RF cable 15 and selectively providing the RF power to the ablation probes 12 via standard RF cables 13 in accordance with a particular pattern, such that each ablation probe 12 is always "on" during a tissue ablation procedure—albeit at a power level that may be substantially below the power level of the RF generator 14.

Figure 2:
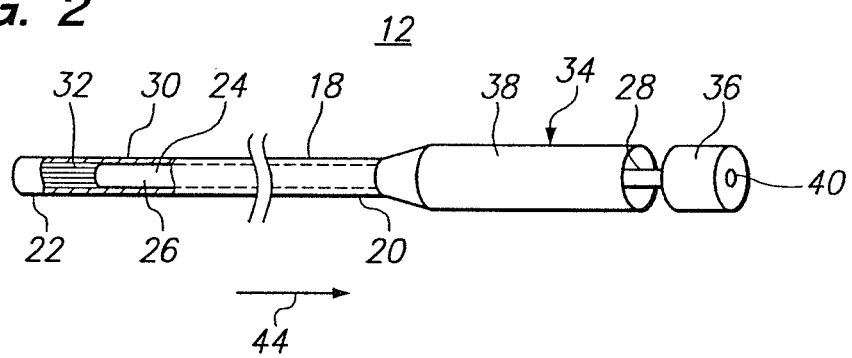
FIG. 2 is a partially cutaway side view of an ablation probe used in the tissue ablation system of FIG. 1, wherein an array of electrode tines is particularly shown retracted.
Figure 3:
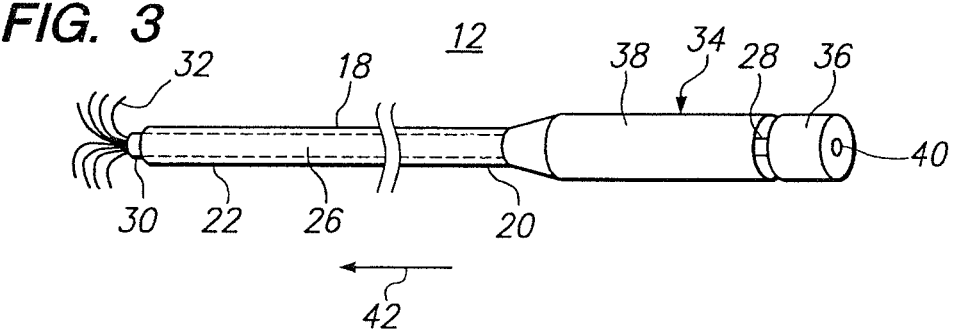
FIG. 3 is a partially cutaway side view of an ablation probe used in the tissue ablation system of FIG. 1, wherein an array of electrode tines is particularly shown deployed.

Referring specifically now to FIGS. 2 and 3, each probe 12 includes an elongate cannula 18 having a proximal end 20, a distal end 22, and a central lumen 24, a probe shaft 26 slidably disposed within the cannula lumen 24 and having a proximal end 28 and a distal end 30, and an array of electrode tines 32 carried by the distal end 28 of the probe shaft 26. The cannula 18 may be rigid, semi-rigid, or flexible depending upon the designed means for introducing the cannula 18 to the target tissue. The probe shaft 26 is composed of a suitably rigid material, such as plastic, metal or the like.

Each probe 12 further includes a handle assembly 34, which includes a handle member 36 mounted to the proximal end 26 of the probe shaft 26, and a handle sleeve 38 mounted to the proximal end 20 of the cannula 18. The handle member 36 is slidably engaged with the handle sleeve 38 (and the cannula 18). The handle member 36 and handle sleeve 38 can be composed of any suitable rigid material, such as, e.g., metal, plastic, or the like. The handle assembly 34 also includes an electrical connector 40 mounted within the handle member 36. The electrical connector 40 is electrically coupled to the electrode array 32, e.g., via the probe shaft 26 (which will be electrically conductive) or separate wires (not shown). The electrical connector 40 is configured for mating with the proximal end of a RF cable 13 (shown in FIG. 1). Alternatively, the RF cable 13 may be hardwired within the handle member 36.

It can be appreciated that longitudinal translation of the probe shaft 26 relative to the cannula 18 in a distal direction 42, by holding the handle sleeve 38 and displacing the handle member 36 in the distal direction 42, deploys the electrode array 32 from the distal end 22 of the cannula 18 (FIG. 3), and longitudinal translation of the probe shaft 26 relative to the cannula 18 in a proximal direction 44, by holding the handle sleeve 38 and displacing the handle member 36 in the proximal direction 44, retracts the probe shaft 26 and the electrode array 32 into the distal end 22 of the cannula 18 (FIG. 2).

In the illustrated embodiment, the RF current is delivered to the electrode array 32 in a monopolar fashion, which means that current will pass from the electrode array 32, which is configured to concentrate the energy flux in order to have an injurious effect on the surrounding tissue, and a dispersive electrode (not shown), which is located remotely from the electrode array 32 and has a sufficiently large area (typically 130 cm_sup_2 for an adult), so that the current density is low and non-injurious to surrounding tissue. In the illustrated embodiment, the dispersive electrode may be attached externally to the patient, e.g., using a contact pad placed on the patient's flank.

Further details regarding electrode array-type probe arrangements are disclosed in U.S. Pat. No. 6,379,353, which is hereby expressly incorporated by reference. It should be noted that the tissue ablation probe 12 illustrated in FIGS. 2 and 3 is only one type of ablation probe that can be used with the tissue treatment system 10. For example, a single needle electrode probe may be used as well.

Referring back to FIG. 1, the RF generator 14 may be a conventional general purpose electrosurgical power supply operating at a frequency in the range from 300 kHz to 5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 50 W to 300 W, usually having a sinusoidal wave form, but other wave forms would also be acceptable. Power supplies capable of operating within these ranges are available from commercial vendors, such as Boston Scientific Therapeutics Corporation. Preferred power supplies are model RF-2000 and RF-3000, available from Boston Scientific Corporation.

Referring still to FIG. 1, the power multiplexor 16 comprises a common input connector 17 coupled to an RF output connector 19 of the RF generator 14 via the RF cable 15, and a plurality of output connectors 21 (in this case, three output connectors 21(1)-(3)) coupled to the electrical connectors 40 of the ablation probes 12 via the RF cables 13. Although the power multiplexor 16 is shown external to the RF generator 14, the power multiplexor 16 can alternatively be incorporated into RF generator 14 itself. However, it is believed that an external power multiplexor 16 will allow the tissue ablation system 10 to be more easily implemented with standard RF generators simply by connecting the power multiplexor 16 between the tissue ablation probes 12 and RF generator 14, as well as to provide physicians the flexibility of optionally using the RF generator 14 in a standard manner by directly connecting a single tissue ablation probe 12 to the RF generator 14 without the use of the power multiplexor 16.

In any event, the power multiplexor 16 is configured for splitting the power signal from the output connector 19 of the RF generator 14 into two power signals, substantially attenuating one of the power signals relative to the other power signal, and presenting the power signals to the output connectors 21, and thus, the ablation probes 12 in accordance with a particular pattern in a manner that provides at least some power to all of the ablation probes 12 during any given time period.

Although it is preferred that one of the power signals remains substantially unattenuated, both power signals may be attenuated if desired as long as one of the power signals is substantially more attenuated than the other power signal. For example, after attenuation, the second power signal may be 1-30 dB less than the first power signal, but preferably is 3-6 dB less than the first power signal. For purposes of brevity and clarity, the power signal that exhibits substantially less power than the other power signal will be considered the "attenuated signal" and the signal that exhibits substantially more power than the other signal will be considered the "nominal signal."

It should be noted the power signals will sometimes be described herein as being presented to the output connectors 21, and at other times will be described herein as being delivered to ablation probes 12. When a power signal is described as being presented to an output connector 21, it follows that such power signal will be delivered to an ablation probe 12 connected to the output connector 21. In a similar fashion, when a power signal is described as being delivered to an ablation probe 12, it follows that such power signal is presented to the output connector 21 to which the ablation probe 12 is connected.

The particular pattern followed by the power multiplexor 16 in delivering the power signals to the ablation probes 12 involves sequentially delivering the nominal power signal to different sets of the ablation probes 12, while delivering the attenuated power signal to other sets of the ablation probes 12. In the illustrated embodiment, each set of ablation probes 12 to which the nominal power signal is delivered contains a single ablation probe 12, and thus, each set of ablation probes 12 to which the attenuated power signal is delivered contains the remaining two ablation probes 12.

For example, as illustrated in FIG. 4, the power multiplexor 16 delivers the nominal power signal to the first ablation probe 12(1) during a first time period T1, while delivering the attenuated power signal to the second and third ablation probes 12(2), (3). The power multiplexor 16 then delivers the nominal power signal to the second ablation probe 12(2) during a second time period T2, while delivering the attenuating power signal to the first and third ablation probes 12(1), (3). The power multiplexor 16 then delivers the nominal power signal to the third ablation probe 12(3) during a third time period T3, while delivering the attenuating power signal to the first and second ablation probes 12(1), (2). This pattern is then repeated for subsequent time periods until completion of the ablation procedure. Thus, it can be appreciated that the plurality of ablation probes 12 may be placed within three different ablation states, as illustrated in FIG. 5. The timing of the pattern may be controlled in any one or more of a variety of manners, as will be described in further detail below.

Although the set of ablation probes 12 to which the nominal power signal is delivered is described as containing a single ablation probe, and the set of ablation probes 12 to which the attenuated power signal is delivered is described as containing the remaining two ablation probes, it should be noted that other probe set configurations are possible. For example, the nominal power signal may be sequentially delivered to different pairs of ablation probes 12, while the attenuated power signal is delivered to the remaining ablation probe 12. It should be noted, however, that it is preferred that the nominal power signal be delivered to a single ablation probe at a time in order to maximize the efficiency of the tissue ablation system 10.

Figure 6:
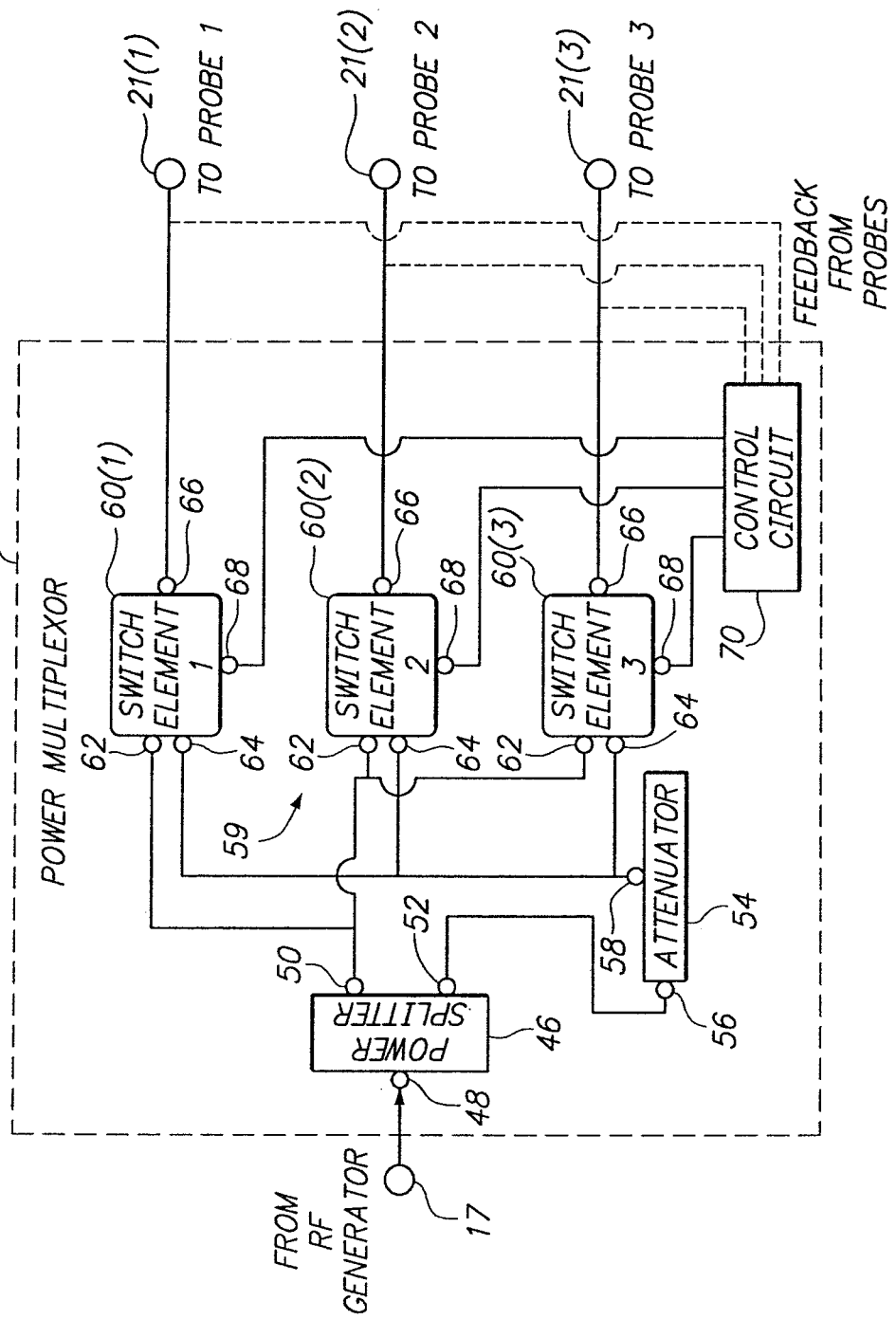
FIG. 6 is a detailed schematic diagram of a power multiplexor used in the tissue ablation system of FIG. 1.

The power multiplexor 16 may be implemented in any one of a variety of manners in order to effect the power signal attenuation and switching functions described above. In the embodiment illustrated in FIG. 6, the power multiplexor 16 comprises a power splitter 46 having a common input terminal 48 coupled to the common input connector 17 of the power multiplexor 16. The power splitter 46 is configured for splitting the power from the RF generator 14, so that it is presented at first and second output terminals 50, 52.

The power multiplexor 16 further comprises a power attenuator 54 having an input terminal 56 coupled to one of the first and second output terminals 50, 52 of the power splitter 46, and an output terminal 58 for presentation of the attenuated power signal. In the illustrated embodiment, the input terminal 56 of the power attenuator 54 is coupled to the second output terminal 52 of the power splitter 46—although the input terminal 56 of the power attenuator 54 can alternatively be coupled to the first output terminal 50 of the power splitter 46 instead. The value of the power attenuator 54 may fall within the range of 1-30 dB, preferably within the range of 3-6 dB. In the illustrated embodiment, the attenuator 54 has a fixed attenuation value, although the attenuation value may alternatively be variable, as discussed in further detail below. Thus, it can be appreciated that the nominal power signal is presented at the first output terminal 50 of the power splitter 46, while the attenuated power signal is presented at the output terminal 58 of the power attenuator 54.

The power multiplexor 16 further comprises a switch device 59 comprising a plurality of switch elements 60 (in this case, three switch elements 60(1)-(3)). Each switch element 60 takes the form of a single-pole double-throw (SPDT) switch element that comprises a first input terminal 62 coupled to the first output terminal 50 of the power splitter 46 for receiving the nominal power signal, and a second input terminal 64 coupled to the output terminal 58 of the attenuator 54 for receiving the attenuated power signal. Each switch element 60 further comprises an output terminal 66 coupled to the respective one of the previously described multiplexed output connectors 21 of the power multiplexor 16 for presentation of either the nominal power signal or the attenuated power signal thereon. That is, the output terminal 66 of the first switch element 60(1) is coupled to the first output connector 21(1), the output terminal 66 of the second switch element 60(2) is coupled to the second output connector 21(2), and the output terminal 66 of the third switch element 60(3) is coupled to the third output connector 21(3). Each switch element 60 comprises a control terminal 68 for changing the respective switch element 60 between two states, the first of which couples the first input terminal 62 to the output terminal 66 to pass the nominal power signal through the switch element 60 to the respective output connector 21 of the power multiplexor 16, the second of which couples the second input terminal 64 to the output terminal 66 to pass the attenuated power signal through the respective switch element 60 to the respective output connector 21 of the power multiplexor 16.

The power multiplexor 16 further comprises a control circuit 70 coupled to the control terminals 68 of the respective switch elements 60 for controlling the timing of the switch elements 60. As previously stated, at any given time, the nominal power signal will be delivered to only one of the ablation probes 12, while the attenuating power signal will be delivered to the remaining ablation probes 12 in accordance with the switching pattern illustrated in FIG. 4. To this end, the control circuit 70 sequentially configures the switch device 59 between three different states by configuring each switch element 60 to pass the nominal power signal to the respective output connector 21, while configuring the remaining switch elements 60 to pass the attenuated power signal to the remaining respective output connectors 21.

That is, the control circuit 70 configures the switch device 59 in a first state by configuring the first switch element 60(1) to pass the nominal power signal to the first output connector 21(1), while configuring the second and third switch elements 60(2), (3) to pass the attenuated power signal to the second and third output connectors 21(2), (3). The control circuit 70 configures the switch device 59 in a second state by configuring the second switch element 60(2) to pass the nominal power signal to the second output connector 21(2), while configuring the first and third switch elements 60(1), (3) to pass the attenuated power signal to the first and third output connectors 21(1), (3). The control circuit 70 configures the switch device 59 in a third state by configuring the third switch element 60(3) to pass the nominal power signal to the third output connector 21(3), while configuring the first and second switch elements 60(1), (2) to pass the attenuated power signal to the first and second output connectors 21(1), (2).

It should be noted that sequential configuration of the switch elements 60 to pass the nominal power signal to the respective output connector 21, and thus, the respective ablation probe 12, does not necessarily mean that the switch elements 60 are so configured in a numerical order, i.e., 1, 2, 3, etc. For instance, the first switch element 60 can be configured to pass the nominal power signal to the first output connector 21, then the third switch element 60, and then the second switch element 60.

The control circuit 70 may be configured to control the timing of the switch device 59 in any one of a variety of manners. In the illustrated embodiment, the control circuit 70 is configured for switching the state of the switch device 59 at a fixed frequency. Preferably, the fixed frequency is at least once every second to maximize the efficiency of the tissue ablation system 10, but less than once every thirty seconds to prevent tissue charring otherwise resulting from providing nominal power to an ablation probe for too long. The control circuit 70 may base the switch timing on the operating frequency of the power signal. For example, if the operating frequency is 300 KHz, and it is desired to change the state of the switch device 59 once a second, the control circuit 70 will change the state of the switch device 59 once every 300K cycles. Of course, rather than basing the switching frequency on digital references, such as clock cycles, the switching frequency may be based on analog references, such as capacitor discharge times.

Alternatively, the control circuit 70 may be configured to change the state of the switch device 59 at a variable frequency. For example, the control circuit 70 may change the state of the switch device 59 based on physiological parameters, such as temperature or impedance, that can be sensed and delivered back to the control circuit 70 during the ablation process (shown as dashed lines in FIG. 6). In the case of an impedance measurement, the control circuit can be connected to an electrode (not shown) on each ablation probe 12 and the dispersive electrode to determine the impedance of the intervening tissue. In this case of a temperature measurement, a temperature sensor, such as a thermistor or thermocouple (not shown) can be mounted to an electrode of each ablation probe 12 and then coupled to the control circuit 70.

In contrast to changing the state of the switch device 59 at a fixed frequency, which may not optimal if the state of the switch device 59 is changed to late or too early, the use of sensed physiological feedback to the control circuit 70 allows the state of the switch device 59 to be changed at the exact time that it needs to be changed. For example, as the measured tissue impedance adjacent an ablation probe 12 that is currently delivered with the nominal power signal begins to exponentially increase or the measured temperature of the tissue adjacent the ablation probe 12 approaches 100_degree_C., thereby indicating that full tissue ablation has been achieved, the control circuit 70 may change the state of the switch device 59, so that the nominal power signal is delivered to the next ablation probe 12, and attenuated power signal is delivered to the previous ablation probe 12, along with the other remaining ablation probe 12. The control circuit 70 can then change the state of the switch device 59 based on the measured impedance and/or temperature adjacent the next ablation probe 12 in the same manner, and so on.

It should be noted that the use of physiological feedback parameters can be used with other probe switching implantations besides those that ensure that power is continuously delivered to each ablation probe. For example, such a feature can be applied to prior art probe switching implementation, wherein power is delivered to one probe at a time, while no power is delivered to the remaining probes.

Although the attenuation value of the attenuator 54 has been described as being fixed, the power multiplexor 16 may be configured to vary the amplitude of the attenuated power signal delivered to the ablation probes 12. In this case, the attenuator 54 has a variable attenuation value that is controlled by the control circuit 70 based on a user input. For example, the power multiplexor 16 may have an attenuation control device (not shown) that can be manipulated by the user based on the characteristics of the tissue to be ablated, e.g., by inputting the attenuation value or by inputting the type of tissue to be ablated. For example, if the tissue is lung tissue, which requires a relatively small amount of power to ablate, the user may input a relatively large attenuation value or simply input the tissue type into the attenuation control device. In contrast, if the tissue is liver tissue or otherwise tissue that is highly vascular, the user may input a relatively small attenuation value or simply input the tissue type into the attenuation control device. Whether the attenuation value is increased or decreased, the control circuit 70 will then respond to whichever type of input is used by varying the attenuation value of the attenuator 54.

Rather than basing the control of the attenuation value on a manual input from the user, the attenuation value may be varied based on a measured physiological parameter, such as tissue impedance or temperature, in order to suit a longer probe dwell time, potentially resulting in a larger ablation. For example, if the measured tissue impedance adjacent an ablation probe 12 to which the attenuated power signal is currently delivered is relatively low or the measured temperature of such tissue is much less than 100_degree_C., tissue ablation will not likely occur in a relatively short time, and therefore, the control circuit 70 may automatically decrease the attenuation value of the attenuator 54, so that the amplitude of the attenuated power signal is increased in order to quickly reach the point at which tissue ablation occurs, thereby decreasing the elapsed time of the ablation procedure. In contrast, as the measured tissue impedance adjacent an ablation probe 12 to which the attenuated power signal is currently delivered begins to exponentially increase or the measured temperature of the tissue adjacent the ablation probe 12 approaches 100_degree_C., the control circuit 70 may automatically increase the attenuation value of the attenuator 54, so that the amplitude of the attenuated power signal is decreased, thereby allowing the ablation probes 12 to have a longer dwell time, potentially creating a larger ablation.

The power multiplexor 16 can be implemented in any suitable manner that facilitates the afore-described attenuation and switching functions. In the illustrated embodiment, the attenuator 54 may be a discrete component that can be obtained from supplier, such as from JFW Industries, Inc. The switch 59 and control circuit 70 can be implemented as a low power switching circuit to minimize the cost of the power multiplexor 16. For example, the switch elements 60 take the form of powered transistors, and the control circuit can take the form of logic circuitry. Alternatively, the switch elements 60 can take the form of discrete components or electromechanical devices, such as relays.

Figures 7, 9:
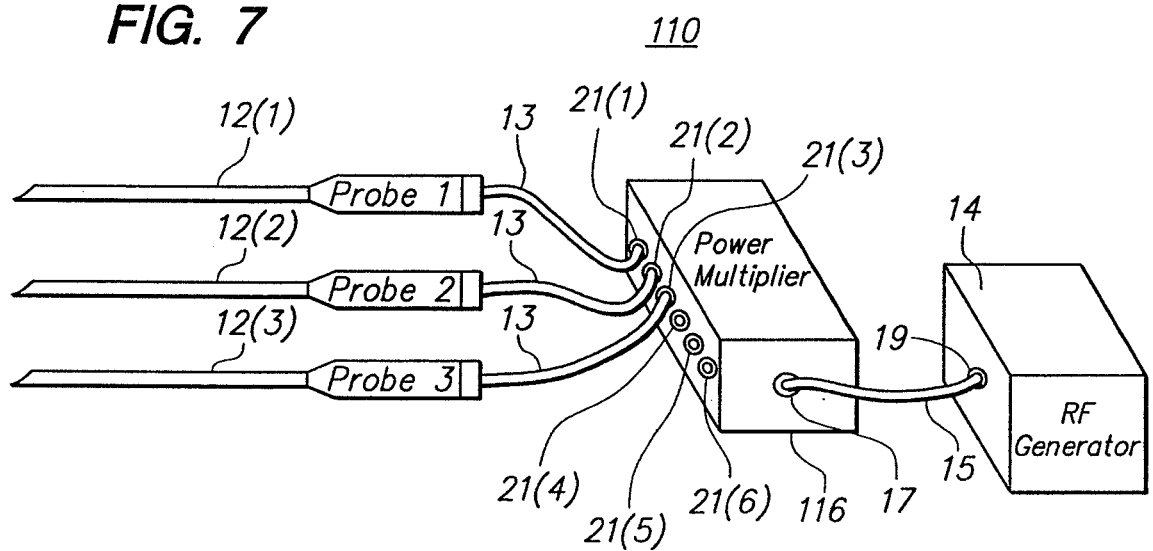
FIG. 7 is a perspective view of a tissue ablation system constructed in accordance with another preferred embodiment of the present invention.
FIG. 9 is a table illustrating the ablation states in which the plurality of tissue ablation probes used in the tissue ablation system of FIG. 7 can be placed.

Although the tissue treatment system 10 has been described as comprising an equal number of ablation probes 12 and output connectors 21, a tissue treatment system can optionally be configured, such that the number of ablation probes used can be less than the number of output ports available. For example, FIG. 7 illustrates a tissue treatment system 110 that is similar to the previously described tissue treatment system 10, with the exception that it comprises a power multiplexor 116 with six output connectors 21(1)-(6), although only three ablation probes 12 are still used in this scenario.

The particular pattern followed by the power multiplexor 116 in delivering the power signals to the ablation probes 12 will depend on the number of used output connectors 21; i.e., the number of output connectors 21 to which ablation probes 12 are connected. The power multiplexor 116 will activate only those output connectors 21 that are used (in this case, output connectors 21(1)-(3)) and sequentially change as many ablation states of the plurality of ablation probes 12 as there are activated output connectors 21. The power multiplexor 116 will only sequentially change three ablation states of the ablation probes 12, which will be accomplished in the same manner illustrated in FIG. 5, and will deliver the nominal and attenuated power signals to the ablation probes 12 in the same manner illustrated in FIG. 4.

If additional ablation probes 12 are used, thereby using additional output connectors 21, the power multiplexor 166 will add additional ablation states between which the ablation probes 12 will change. For example, if three additional ablation probes 12 are added, thereby using all six output connectors 21, the power multiplexor 166 will sequentially change six ablation states of the ablation probes 12 in accordance with the switching pattern illustrated in FIG. 9, and will deliver nominal and attenuated power signals to the six ablation probes 12 connected to the used output connectors 21 in a manner similar to that previously described, with the exception that nominal power signal will be delivered to each of the six ablation probes 12, while delivering the attenuated power signal to the remaining five ablation probes.

Figure 8:
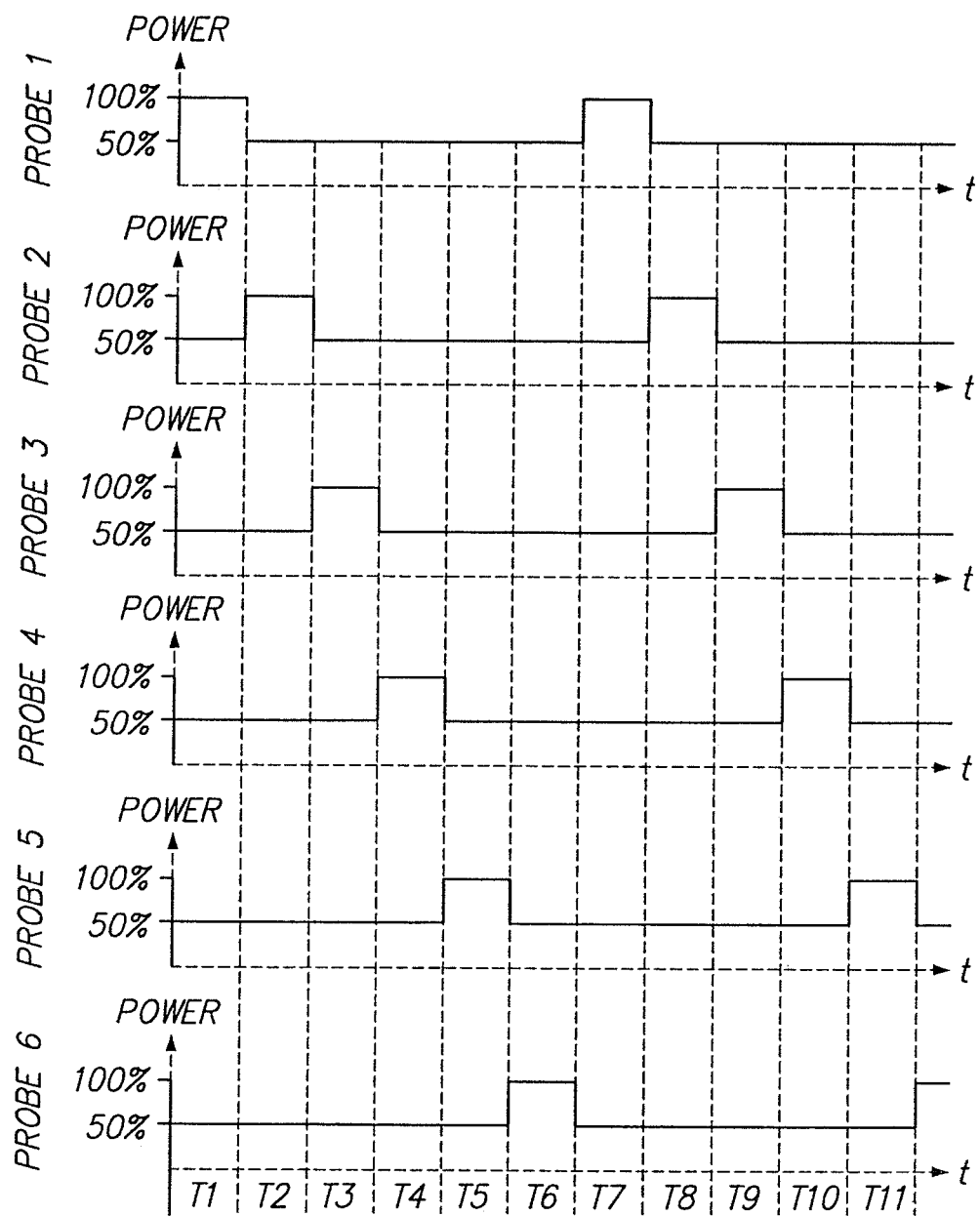
FIG. 8 is a timing diagram illustrating the switching of ablation energy between tissue ablation probes used in the tissue ablation system of FIG. 7.

That is, as illustrated in FIG. 8, the power multiplexor 116 delivers the nominal power signal to the first ablation probe 12(1) during a first time period T1, while delivering the attenuated power signal to the second to sixth ablation probes 12(2)-(6). The power multiplexor 116 then delivers the nominal power signal to the second ablation probe 12(2) during a second time period T2, while delivering the attenuating power signal to the first and third through fifth ablation probes 12(1), (3)-(6). This switching pattern continues for time periods T3-T6 and continuously repeats until the ablation procedure is completed.

Figure 10:
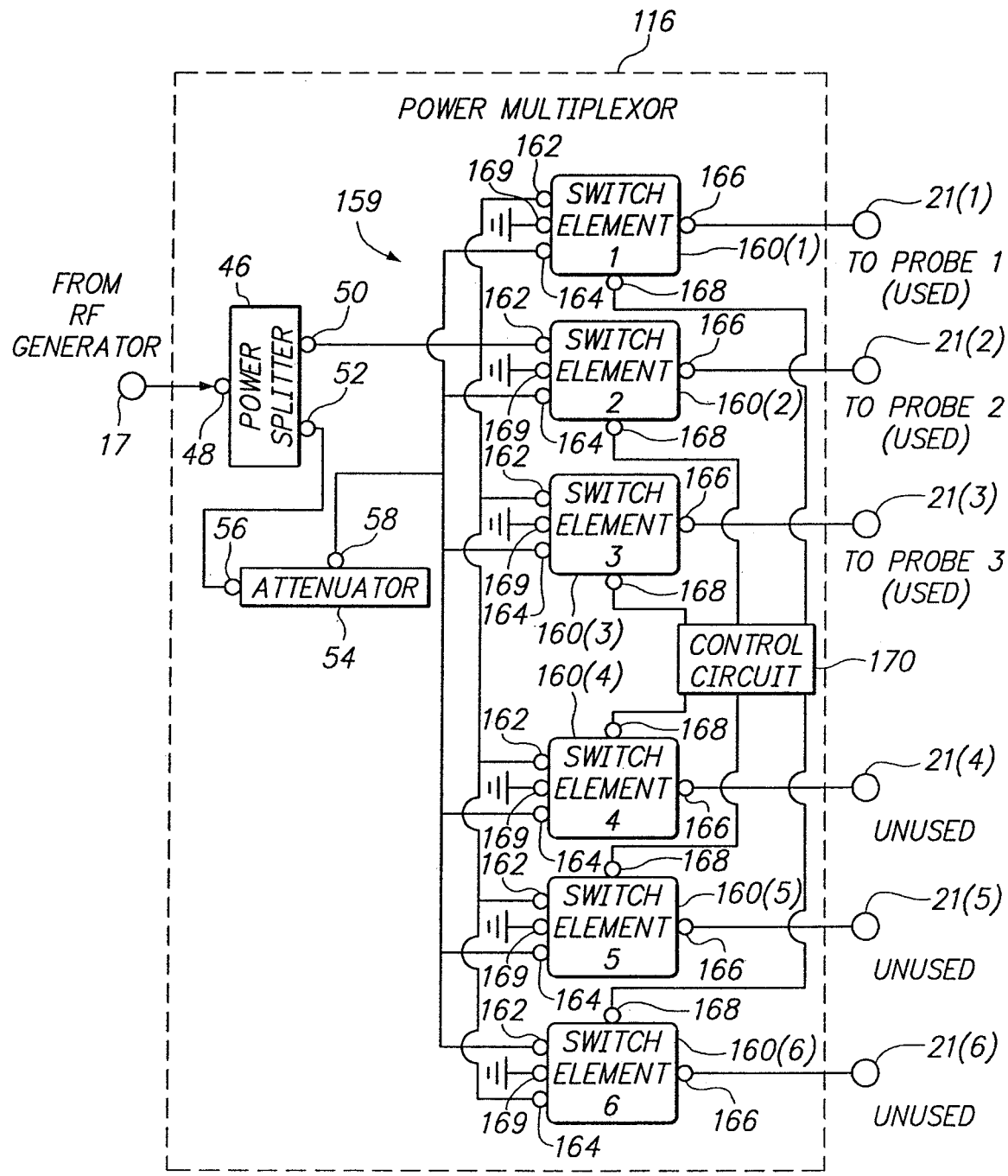
FIG. 10 is a detailed schematic diagram of a power multiplexor used in the tissue ablation system of FIG. 7.

The power multiplexor 116 may be implemented in the same manner as the power multiplexor 16, with the exception that the power multiplexor 116 comprises a switch 159 having six single pole three position (SP3P) switching elements 160. In particular, like the previously described switching elements 60, each of the switching elements 160 illustrated in FIG. 10 comprises a first input terminal 162 coupled to the first output terminal 50 of the power splitter 46 for receiving the nominal power signal, and a second input terminal 164 coupled to the output terminal 58 of the power attenuator 54 for receiving the attenuated power signal. Unlike the previously described switching elements 60, each of the switching elements 160 comprises a third input terminal 169 coupled to ground.

Each switch element 160 also comprises a control terminal 168 for changing the switch element 160 between three states, the first two of which are similar to the states in which the previously described switch elements 60 can be placed. That is, each switch element 160 can be placed in a first state that connects the first input terminal 162 to the output terminal 166 to pass the nominal power signal through the switch element 160 to the respective output connector 21, and a second state that connects the second input terminal 164 to the output terminal 166 to pass the attenuated power signal through the switch element 160 to the respective output connector 21. Unlike the previously described switch elements 60, each switch element 160 can be placed in a third state that connects the grounded third input terminal 169 to the output terminal 166 to prevent the passing of any power signal through the respective switch element 160 to the respective output connector 21. As a result, the switch element 160 and the respective output connector 21 are deactivated.

The power multiplexor 16 also comprises a control circuit 170 that is similar to the previously described control circuit 70, with the exception that the control circuit 170 is configured to activate the used output connectors 21 by passing one of the nominal or attenuated power signals through the respective switch elements 160, and to deactivate the unused output connectors 21 by grounding the respective switch elements 160. As discussed above, the control circuit 170 will sequentially change as many states of the switch device 159 as there are used output connectors 21.

In this case, the control circuit 170 will sequentially configure the switch device 159 between three different states by configuring each of the first three switch elements 160(1)-(3) to pass the nominal power signal to the respective one of the output connectors 21(1)-(3), while configuring the remaining switch elements 160(1)-(3) to pass the attenuated power signal to the remaining respective output connectors 21(1)-(3). The control circuit 170 will effectively accomplish this function in the same manner that the control circuit 70 sequentially configured the switch device 59 described above. The main difference is that the control circuit 170 will ground the switch elements 160(4)-(6) to prevent the passage of either the nominal power signal or the attenuated power signal to the respective output terminals 21(4)-(6). If additional ablation probes 12 are added, thereby using additional output connectors 21, the control circuit 170 will configure the switch 159 with additional states, allowing either of the nominal power signal or the attenuated power signal to pass through the switch elements 160 to the additional output connectors 21.

The control circuit 170 can determine the number of used output connectors 21 in any one of a variety of manners. For example, the power multiplexor 16 can be provided with a user control (not shown) that allows the user to manually set the number of ablation probes 12, and thus, output connectors 21, to be used. In this case, the user will have to mate the ablation probes 12 to the output connectors 21 in a predetermined pattern. For example, if n number of ablation probes 12 are to be used, the user will have to mate the ablation probes with the first n output connectors 21 of the power multiplexor 16. The control circuit 70 is configured to respond to the user entry of number of ablation probes 12 by activating the first n output connectors 21.

Alternatively, the control circuit 170 can be configured to automatically sense the output connectors 21 that are to be used when the ablation probes 12 are mated with these output connectors 21. For example, mating of an ablation probe 12 to an output connector 21 may initiate a closed circuit condition that can be sensed by the control circuit 170. Accordingly, the control circuit 170 can then be configured to activate the output connector 21 by grounding it through the switch element 160 when the closed circuit condition is sensed. In contrast, removal of an ablation probe 12 from an output connector 21 may initiate an open circuit condition that can be sensed by the control circuit 170. Accordingly, the control circuit 170 can then be configured to deactivate the output connector 21 by grounding it through the switch element 160 when the open circuit condition is sensed. Notably, in this case, the user need not mate the ablation probes 12 to the output connectors 21 in a predetermined pattern, since the control circuit 70 can automatically sense the output connectors 21 that are to be used.

It should be noted that the adaptable probe activation feature can be used with other probe switching implantations besides those that ensure that power is continuously delivered to each ablation probe. For example, such a feature can be applied to prior art probe switching implementation, wherein power is delivered to one probe at a time, while no power is delivered to the remaining probes.

It should also be noted that although the previously described tissue ablation systems 10, 110 have been described as being mono-polar ablation systems, the attenuation-switching functions described above can be applied to bipolar ablation systems. In these types of systems, RF current is delivered to the electrode tines in a bipolar fashion, which means that current will pass between two electrode tines ("positive" and "negative" electrodes) of a single ablation probe, or between the electrode tines of the two different ablation probes. In the former case, the tissue ablation system will generally perform the attenuation and switching functions in the same manner described above. In the latter case, some of the output connectors will operate as positive poles to which nominal or attenuated power signals are presented and delivered to the connected ablation probes, and some of the output connectors on the power multiplexor will be act as negative poles from which nominal or attenuated power signals are received from the connected ablation probes after passage through intervening tissue.

Although the previous tissue ablation systems 10, 110 have been described as providing power to the ablation probes using a single RF source, it should be noted that multiple RF sources can be used to provide the same attenuation and switching functions as a single RF source—although such multiple RF sources may require more complex timing circuitry in order to coordinate the different functions of the RF sources.

For example, one RF generator can be used to sequentially delivered nominal power signal to ablation probes, while delivering no power signal to the remaining ablation probes to which the nominal power signal is currently not being delivered. In this case, a power multiplexor with no attenuation feature can be used to switch power between the ablation probes. Another RF generator can be used to deliver attenuated power signal to the ablation probes that are currently not being delivered power from the first RF generator. Control circuitry is preferably used to coordinate the timing of both RF generators, so that when the nominal power signal is delivered to one ablation probe, the attenuated power signal is delivered to the other ablation probes.

As another example, a number of RF generators equal to the number of ablation probes can be used. In this case, each RF generator is dedicated to an ablation probe, and alternately provides nominal and attenuated power signals to that ablation probe. Control circuitry is used to maintain a phase difference between the RF generators, so that the nominal power signal is sequentially delivered to each ablation probe, while the attenuated power signal is delivered to the remaining ablation probes to which the nominal power signal is currently not being delivered.

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 $cm^3$ to 150 $cm^3$, and often from 2 $cm^3$ to 35 $cm^3$. However, the use of multiple ablation probes lends itself to either the treatment of relatively large tumors or a multiplicity of smaller tumors distributed within the patient's body. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 11A:
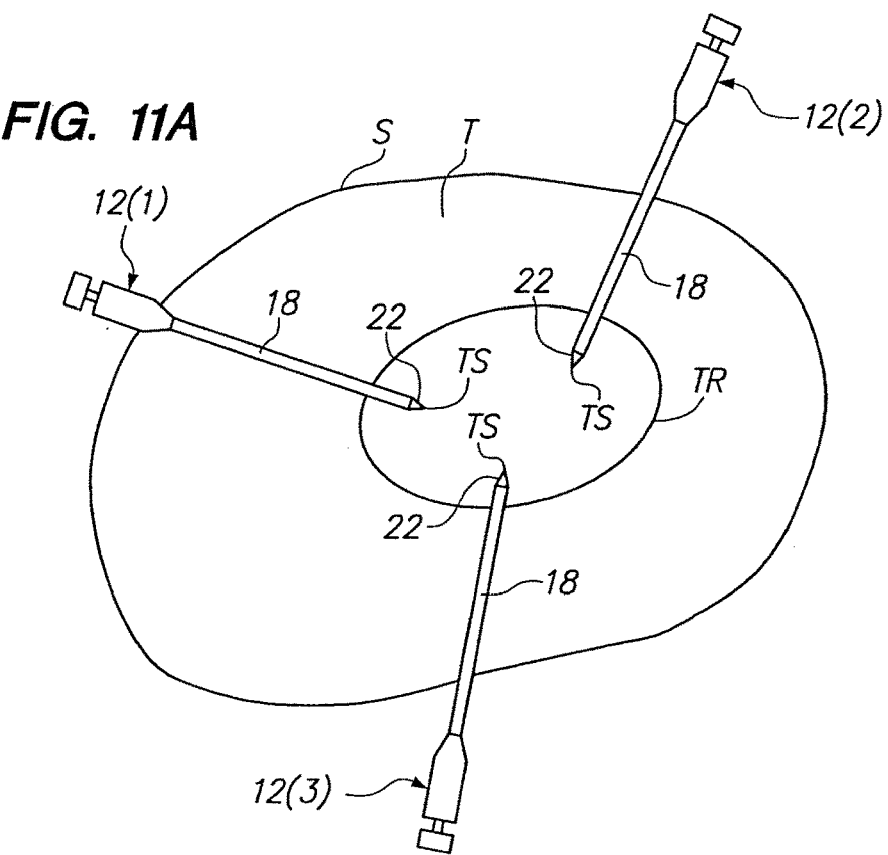
FIGS. 11A-11F are side views illustrating a method of ablating tissue using the tissue ablation system of FIG. 1.

Referring now to FIGS. 11A-11F, the operation of the tissue ablation system 10 is described in treating a treatment region TR within tissue T located beneath the skin or an organ surface S of a patient. Although a single treatment region TR is illustrated for purposes of brevity, the tissue ablation system 10 may alternatively be used to treat multiple treatment regions TR. The ablation probes 12 are first introduced through the tissue T, so that the distal ends 22 of the cannulae 18 are located respective target sites TS within the treatment region TR (FIG. 11A).

This can be accomplished using any one of a variety of techniques. In the preferred method, each ablation probe 12 is percutaneously introduced to the treatment region TR directly through the patient's skin or through an open surgical incision. In this case, the distal ends of the cannulae 18 may be sharpened to facilitates introduction of the ablation probes 12 to the treatment region TR. In such cases, it is desirable that each cannula 18 be sufficiently rigid, i.e., have a sufficient column strength, so that it can be accurately advanced through tissue T. In other cases, each cannula 18 may be introduced using an internal stylet that is subsequently exchanged for the probe shaft 26. In this latter case, the probe shaft 26 can be relatively flexible, since the initial column strength will be provided by the stylet. More alternatively, a component or element may be provided for introducing each cannula 18 to the respective target ablation site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 18 can then be introduced through the sheath lumen, so that the distal end 22 of the cannula 18 advances from the sheath into the target ablation site TS.

Figure 11B:
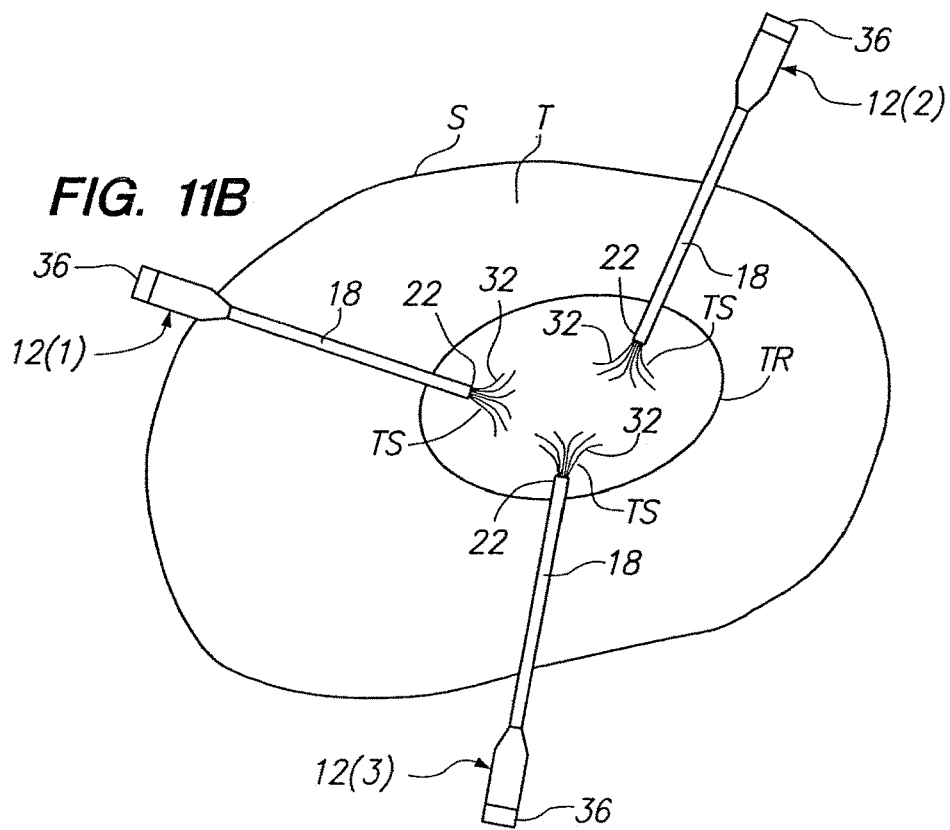

Once the ablation probes 12 are properly positioned, the handle member 36 of each ablation probe 12 is distally advanced to deploy the electrode array 32 radially outward from the distal end 22 of the respective cannula 18 until the electrode array 32 fully everts within the respective target tissue site TS (FIG. 11B).

Once the electrode arrays 32 are fully deployed into the respective target ablation sites TS, the RF generator 14 is connected to the ablation probes 12 through the power multiplexor 16 (shown in FIG. 1). In accordance with the switching pattern illustrated in FIG. 4, the RF generator 14 and power multiplexor 16 are then operated to sequentially delivering nominal ablation energy (in this case, the nominal power signal) to the ablation probes 12, while delivering the attenuated ablation energy (in this case, the attenuated power signal) to the ablation probes 12 currently not delivered with the nominal ablation energy. In other words, the ablation states of the ablation probes 12 are sequentially changed in accordance with the states illustrated in FIG. 5.

Figure 11C:
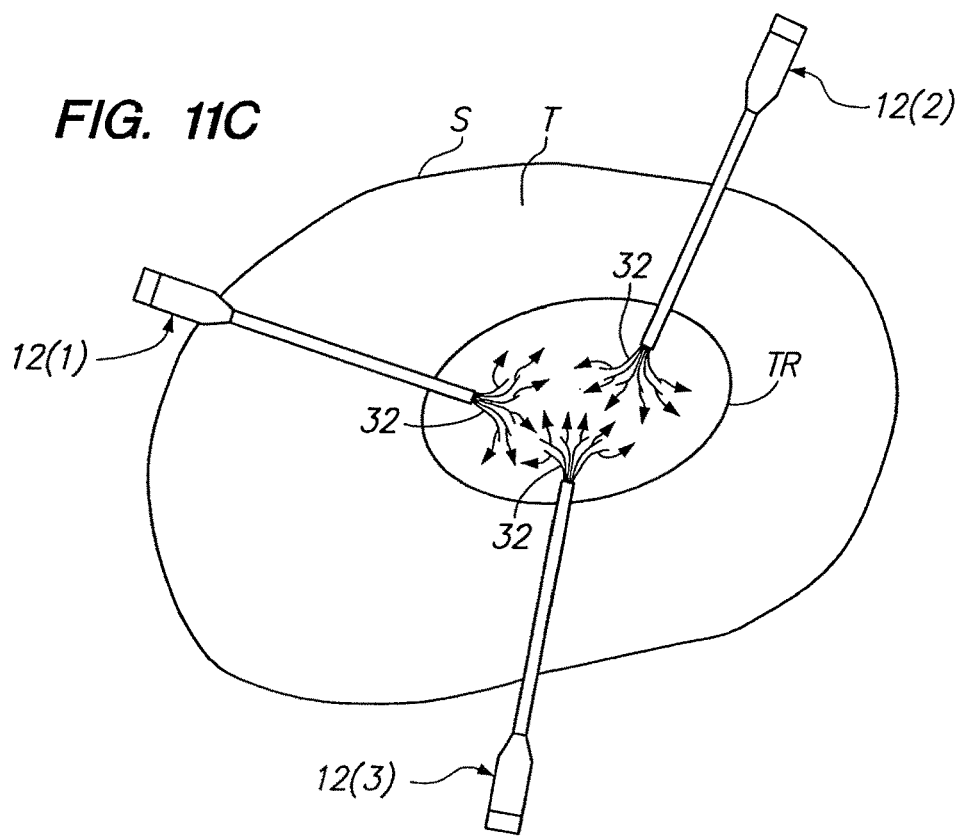
Figure 11D:
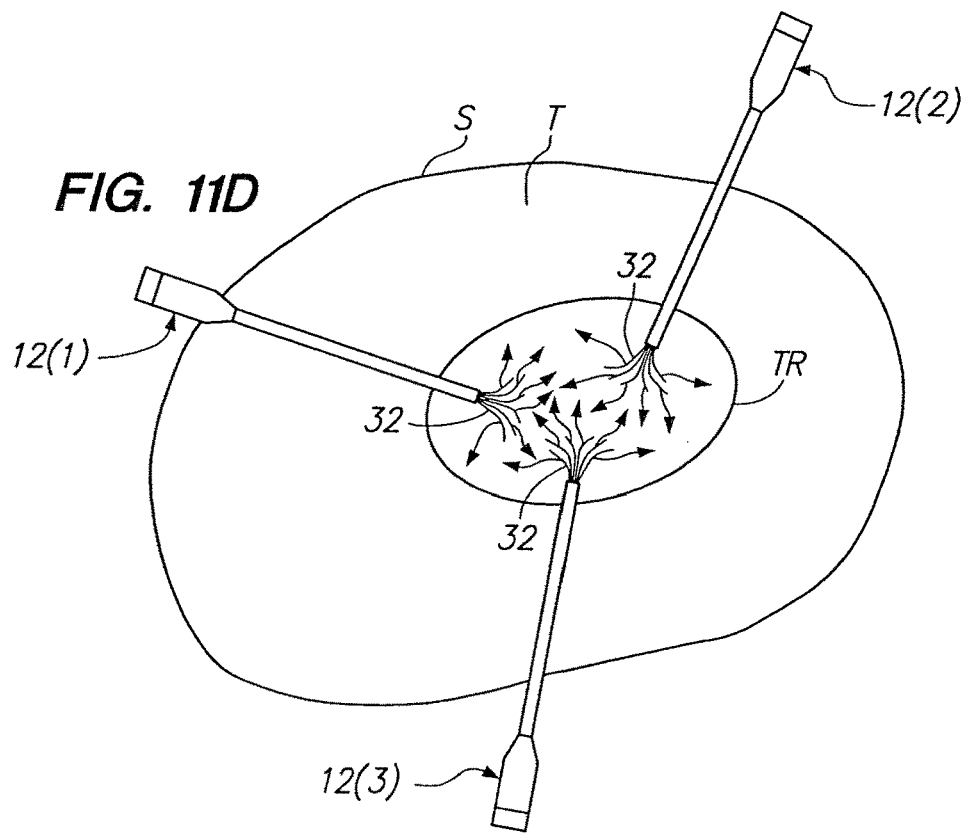
Figure 11E:
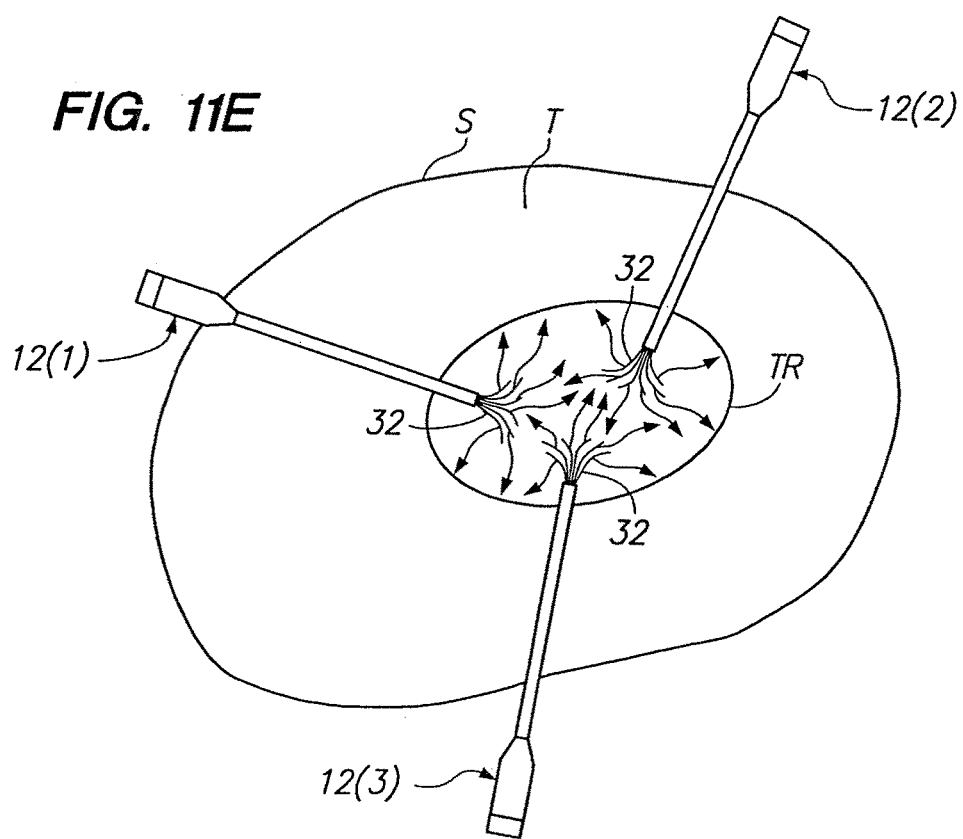
Figure 11F:
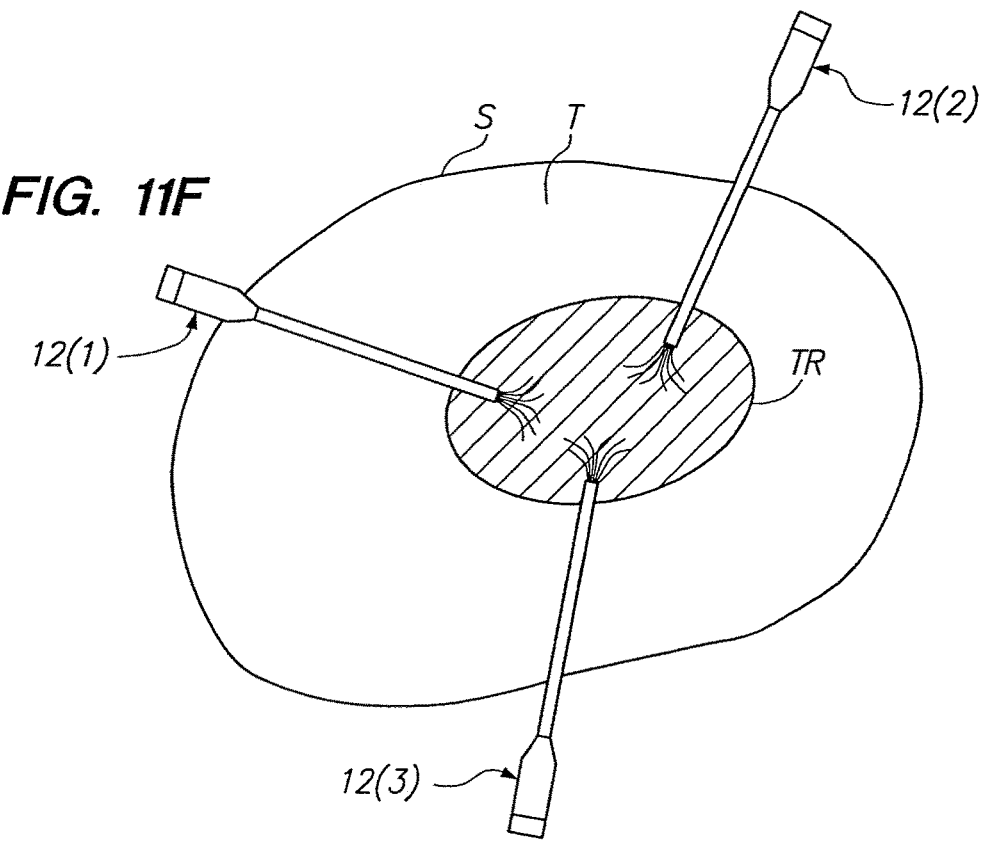

In particular, the power multiplexor 16 places the ablation probes 12 into the first ablation state by delivering the nominal ablation energy to the first ablation probe 12(1) to convey a relatively great amount of ablation energy into the tissue adjacent the first ablation probe 12(1), and by delivering the attenuated ablation energy to the second and third ablation probes 12(2), (3) to convey a relatively small amount of ablation energy into the tissue adjacent the second and third ablation probes 12(2), (3) (FIG. 11C). After a fixed period of time, or alternatively, after a measured physiological parameter indicates a change is necessary, the power multiplexor 16 places the ablation probes 12 into the second ablation state by delivering the nominal ablation energy to the second ablation probe 12(2) to convey a relatively great amount of ablation energy into the tissue adjacent the second ablation probe 12(2), and by delivering the attenuated ablation energy to the first and third ablation probes 12(1), (3) to convey a relatively small amount of ablation energy into the tissue adjacent the first and third ablation probes 12(1), (3) (FIG. 11D). After a fixed period of time or after a measured physiological parameter indicates a change is necessary, the power multiplexor 16 places the ablation probes 12 into the third ablation state by delivering the nominal ablation energy to the third ablation probe 12(3) to convey a relatively great amount of ablation energy into the tissue adjacent the third ablation probe 12(3), and by delivering the attenuated ablation energy to the first and second ablation probes 12(1), (2) to convey a relatively small amount of ablation energy into the tissue adjacent the first and third ablation probes 12(1), (2) (FIG. 11E). The steps in FIGS. 11C-11E are repeated until the treatment region TR is completely ablated (FIG. 11F).

In an optional method, if the tissue ablation system 10 has a variable attenuation feature, the attenuation value of the power attenuator 54 within the power multiplexor 16 may be manually set by the user prior to initiation of the ablation procedure, or automatically and dynamically set by the power multiplexor 16 during the ablation procedure.

Operation of the tissue ablation system 110 will be similar to that of the tissue ablation system 10, with the exception that the power multiplexor 116 will adapt to the number of ablation probes 12 used either after a manual input by the user or by automatically sensing the number of used ablation probes 12.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of treating tissue within a patient, comprising:
   introducing a plurality of ablation probes into a treatment region, the plurality of ablation probes including a first ablation probe and a second ablation probe;
   sequentially delivering nominal and attenuated ablation energy to the first ablation probe and sequentially delivering nominal and attenuated ablation energy to the second ablation probe, wherein the nominal and the attenuated ablation energy to the first and the second ablation probe is delivered using a switch device; and
   ablating the tissue with the nominal ablation energy and attenuated ablation energy.

2. The method of claim 1, wherein the sequential delivery of energy includes delivering nominal ablation energy to the first ablation probe while delivering attenuated ablation energy to the second ablation probe, and subsequently delivering attenuated ablation energy to the first ablation probe while delivering nominal ablation energy to the second ablation probe.

3. The method of claim 1, wherein the attenuated ablation energy is at least 3 dB below the nominal ablation energy.

4. The method of claim 1, further comprising generating a common power signal, by an ablation source, and splitting the common power signal into first and second power signals, wherein the first power signal is the nominal ablation energy delivered to the first ablation probe and the second power signal is the attenuated ablation energy delivered to the second ablation probe.

5. The method of claim 1, further comprising dynamically varying the attenuation value of the attenuated ablation energy.

6. A method of treating tissue within a patient, comprising:
   introducing a plurality of ablation probes into a treatment region, the plurality of ablation probes including a first ablation probe and a second ablation probe;
   delivering, using a switching device, a pattern of power signals to the plurality of ablation probes, wherein the pattern includes sequentially delivering a first ablation energy and a second ablation energy to the first ablation probe and sequentially delivering the first ablation energy and the second ablation energy to the second ablation probe, wherein the first ablation energy is greater than the second ablation energy; and ablating the treatment region with the first ablation energy and the second ablation energy.

7. The method of claim 6, further comprising repeatedly delivering the first ablation energy to the first ablation probe and repeatedly delivering the second ablation energy to the second ablation probe.

8. The method of claim 6, wherein the first ablation energy and second ablation energy are radiofrequency (RF) ablation energy.

9. The method of claim 6, wherein the pattern comprises sequentially delivering the first ablation energy to the first ablation probe while delivering the second ablation energy to the second ablation probe, followed by delivering the first ablation energy to the second ablation probe while delivering the second ablation energy to the first ablation probe.

10. The method of claim 6, wherein the second ablation energy is in the range of 3-6 dB below the first ablation energy.

11. The method of claim 6, wherein the plurality of ablation probes includes a third ablation probe, and wherein the pattern comprises sequentially delivering the first ablation energy to the first ablation probe, followed by delivering the first ablation energy to the second ablation probe, followed by delivering the first ablation energy to the third ablation probe.

12. A method of treating tissue within a patient, comprising:

introducing a plurality of ablation probes into a treatment region, the plurality of ablation probes including a first ablation probe, a second ablation probe, and a third ablation probe;

delivering, using a switch device, a pattern of power signals to the plurality of ablation probes, wherein the pattern includes sequentially delivering a first ablation energy and a second ablation energy to two or more ablation probes of the plurality of ablation probes while sequentially delivering the first ablation energy and the second ablation energy to another probe within the plurality of probes; and ablating the treatment region with the first ablation energy and the second ablation energy.

13. The method of claim 12, wherein the first ablation energy is greater than the second ablation energy.

14. The method of claim 12, wherein the second ablation energy is at least 3 dB below the first ablation energy.

15. The method of claim 12, wherein the second ablation energy is greater than the first ablation energy.

* * * * *